(12) United States Patent
Mett

(10) Patent No.: US 7,981,266 B2
(45) Date of Patent: Jul. 19, 2011

(54) ELECTROCHEMICAL GAS SENSOR CONTAINING ELECTRIC CONNECTION LINES OR HOUSING CONTACT BRIDGES COMPRISING CARBON NANOTUBES

(75) Inventor: Frank Mett, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 679 days.

(21) Appl. No.: 11/856,228

(22) Filed: Sep. 17, 2007

(65) Prior Publication Data

US 2008/0202930 A1 Aug. 28, 2008

(30) Foreign Application Priority Data

Nov. 22, 2006 (DE) .......................... 10 2006 054 948

(51) Int. Cl.
*G01N 27/407* (2006.01)
(52) U.S. Cl. ...... 204/434; 73/23.31; 73/23.32; 204/431; 204/400; 977/953
(58) Field of Classification Search .......... 204/400–435; 73/23.31, 23.32; 977/953
See application file for complete search history.

(56) References Cited

U.S. PATENT DOCUMENTS

| | | | | |
|---|---|---|---|---|
| 5,302,274 | A * | 4/1994 | Tomantschger et al. | 204/412 |
| 5,865,973 | A * | 2/1999 | Kiesele et al. | 204/415 |
| 6,607,642 | B1 * | 8/2003 | Kiesele et al. | 204/415 |
| 7,077,938 | B1 * | 7/2006 | Austen et al. | 204/431 |
| 2004/0149578 | A1 | 8/2004 | Huang | |
| 2005/0045493 | A1 * | 3/2005 | Mahurin et al. | 205/775 |
| 2005/0186333 | A1 * | 8/2005 | Douglas | 427/97.1 |
| 2006/0017348 | A1 * | 1/2006 | Okubo | 310/253 |
| 2006/0124028 | A1 | 6/2006 | Huang et al. | |

FOREIGN PATENT DOCUMENTS

| | | |
|---|---|---|
| DE | 199 39 011 | 1/2001 |
| EP | 0 762 116 A1 | 3/1997 |
| EP | 1 544 607 A1 | 6/2005 |
| EP | 1596929 A1 | 11/2005 |
| EP | 1810332 A2 | 7/2007 |
| GB | 2353363 A | 2/2001 |
| WO | WO 2004/053893 * | 6/2004 |
| WO | WO2004052447 | 6/2004 |
| WO | WO 2004/114424 * | 12/2004 |
| WO | WO 2005/085824 * | 9/2005 |
| WO | WO2006048845 A2 | 5/2006 |
| WO | WO 2006/090214 A2 | 8/2006 |

OTHER PUBLICATIONS

Baughman et al., Carbon Nanotubes—the Route Toward Applications, (Science Aug. 2, 2002: vol. 297. No. 5582, pp. 787-792).*

* cited by examiner

*Primary Examiner* — Alexa D Neckel
*Assistant Examiner* — Jennifer Dieterle
(74) *Attorney, Agent, or Firm* — McGlew and Tuttle, P.C.

(57) ABSTRACT

An electrochemical gas sensor (9) has improved electrochemical measurement properties and housing tightness for an electrolyte at the sites at which the connection lines (11, 21, 31) pass through. The sensor (9) includes a housing (4), containing at least one measuring electrode (1) and a counterelectrode (2) and with electric connection lines (11, 21, 31) from the electrodes (1, 2, 3) to a measuring unit (8) arranged outside the housing (4). The electric connection lines (11, 21, 31) include carbon nanotubes (CNT, Carbon Nanotubes) at least in some sections in the housing (4) in the area of the electrolyte wetting.

21 Claims, 7 Drawing Sheets

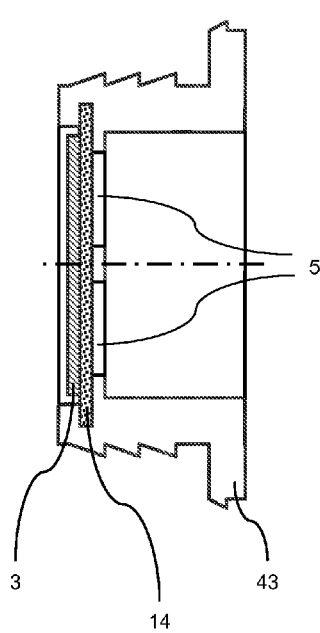
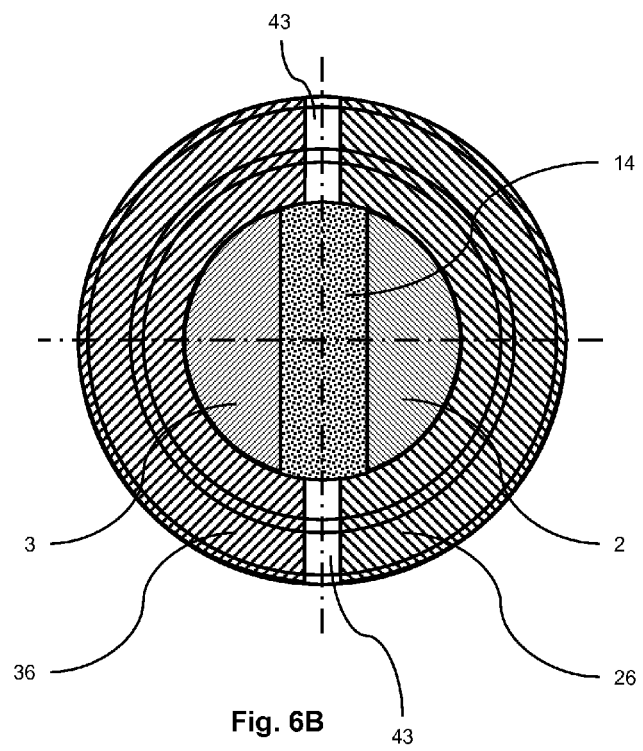
Fig. 6A
Fig. 6B

ELECTROCHEMICAL GAS SENSOR CONTAINING ELECTRIC CONNECTION LINES OR HOUSING CONTACT BRIDGES COMPRISING CARBON NANOTUBES

CROSS REFERENCE TO RELATED APPLICATIONS

This application claims the benefit of priority under 35 U.S.C. §119 of German Patent Application DE 10 2006 054 948.1 filed Nov. 22, 2006, the entire contents of which are incorporated herein by reference.

FIELD OF THE INVENTION

The present invention pertains to an electrochemical gas sensor containing housing parts from carbon nanotubes, which housing parts form electric connection lines or housing contact bridges.

BACKGROUND OF THE INVENTION

Electrochemical gas sensors usually have a housing with at least one measuring electrode and a counterelectrode in an electrolyte and with electric connection lines from the electrodes to a measuring unit arranged, in general, outside the housing, wherein the measuring unit is usually a potentiostat with an evaluating circuit. The connection lines are contacted with the electrodes in the known manner in the form of drain wires made especially of precious metals such as platinum, because these are resistant to the common electrolytes, such as acids, alkalies and salt solutions.

However, a number of drawbacks are also associated with the use of precious metal drain wires. The catalytic activity of the precious metals is utilized in the majority of electrochemical gas sensors for detecting measured gases. These gas sensors are not selective but always detect a plurality of gases due to the high catalytic activity of their measuring electrodes. For the same reason, these sensors have high basic currents as well as signals for air humidity and temperature changes.

The precious metal measuring electrodes of these gas sensors usually have very large active surfaces, on which the reaction of the measured gas or measured gases takes place. The surface of the likewise catalytically active contacting wires, which is small compared to this, therefore makes a nearly unmeasurable contribution to the signal current.

Sensors which no longer detect the gas to be measured directly at the measuring electrode but indirectly via a chemical mediator were therefore developed (DE 19939011 C1) in the trend towards the more sensitive and selective detection of measured gases. Measuring electrodes comprising diamond-like carbon (DLC) are used here, which do not have any catalytic activity, show no cross sensitivity, have extremely low basic currents, and have no signals for a change in the air humidity and temperature. The last, catalytically active component in the area of the measuring electrodes of these gas sensors is the precious metal drain wire, which, acting practically as an electrode, now represents the essential disturbance in respect to the above-described problems.

Even though this situation can be improved by the use of graphite, carbon fibers or glass carbon for contacting the measuring electrode, it cannot be solved, because these materials also have some interfering cross sensitivities, e.g., for nitrogen oxides. Moreover, these materials, which are in contact with the electrolyte, are oxidized over time and lose contact with the measuring electrode.

However, there also are problems concerning the tightness of the connection lines through the housings of such electrochemical gas sensors because, for example, oxygen is formed at the counterelectrode and the contacting wire thereof in oxygen sensors, so that a tightness problem develops at the site at which the contact wire is led through the housing because the plastic surrounding the metal wire and thus exerting a sealing action is progressively degraded by oxidation due to the evolution of gas and the electrolyte can flow out of the housing along the gap thus formed.

Another cause of leaks is the different coefficients of expansion of precious metal wires and the plastic housing, so that capillary gaps, through which the electrolyte can flow out, are formed over time at the openings through which the wire is led out of the housing for this reason as well. To overcome these drawbacks, special liquid and labyrinth sealing systems are used, which are associated with additional working steps and material consumption and continue to cause problems in practice because of the different materials used and the temperature changes occurring.

The alternative use of a conductive composite plastic injected into the sensor housing as a substitute for the draining connection lines has also failed to prove successful because the electric conductivity of these plastics declines over time since the components responsible for the conductivity, such as graphite or carbon fibers, undergo oxidation and thus develop a high ohmic resistance.

US 2005/0186333 A1 discloses an electrochemical measuring arrangement for determining an analyte in an aqueous liquid test sample, in which the measuring electrode comprises an electrically conductive film, which is formed with carbon nanotubes.

SUMMARY OF THE INVENTION

The object of the present invention is to provide an electrochemical gas sensor which is improved in terms of reduced cross sensitivity, a wide potential window and durable electrolyte-tight contacting through or via the housing.

According to the invention, an electrochemical gas sensor is provided with a housing containing at least one measuring electrode and a counterelectrode in electrolyte contact. The sensor has electric connection elements. The electric connection elements are formed as electric connection lines or as housing contact bridges from the electrodes to a measuring unit arranged outside the housing. The electric connection lines comprise carbon nanotubes with at least some of the connection lines either consisting essentially of carbon nanotubes or containing carbon nanotubes. The carbon nanotube electric connection lines may be in some sections in the housing in the area of the electrolyte wetting and/or the housing parts forming housing contact bridges.

The essential advantage of the electrochemical gas sensor according to the present invention with connection elements, which are designed as electric connection lines or as housing contact bridges and which consist or contain carbon nanotubes (CNT), is that with good electrical conductivity, the catalytic activity is substantially lower than in the case of precious metals and the carbon fibers used hitherto to achieve electric conductivity in housing parts made of plastics, while the potential window is wide at the same time, so that evolution of gas, which reduces tightness, can appear at substantially higher potentials only. On the whole, a substantially improved, electrolyte-tight contacting through the housing or contacting via the housing of the gas sensor is thus possible.

The carbon nanotubes employed are used in the form of filaments, films or strips and preferably consist of single-wall, metallically conductive carbon nanotubes (SWNCT, Single Wall Carbon Nanotubes). As an alternative, the carbon nanotubes form the connection lines combined with a plastic as a composite component.

As an alternative, parts of the housing are designed as electric connection elements between the electrodes and drain points outside the housing, the housing parts containing carbon nanotubes.

It is essential for all claimed embodiments of the gas sensor that some of the connection lines or corresponding housing parts consist essentially of carbon nanotubes or contain same at least in some sections in the area of the contacting with the electrodes and preferably also in the line section wetted with the electrolyte and also preferably from the electrodes to the passage through the housing to the outside. The filament-, film- or strip-shaped connection lines comprising carbon nanotubes can be preferably applied to the housing parts, especially on the films of a flat gas sensor, which films form the housing, by means of an ink jet printing method. The electric connection lines may be formed from carbon nanotubes in the form of films, mats, strips or filaments, especially combined with a plastic as a composite component.

Although the electric connection lines may consist of or contain carbon nanotubes in the area of the housing it may be advantageous that only the sections of the connection lines that are in contact with the electrolyte consist of carbon nanotubes or contain carbon nanotubes.

The carbon nanotubes may preferably be single-wall carbon nanotubes (SWCNT). However, the carbon nanotubes may be multi-wall carbon nanotubes (MWCNT).

At least one of the electrodes of the electro chemical gas sensor may be provided with a diffusion membrane. A diaphragm for liming the entry of gas to be measured from the environment may be present.

The measuring electrode may consist of multi-wall carbon nanotubes (MWCNT), preferably combined with a plastic as a binder, especially with Teflon. The measuring electrode may comprise single-wall or double-wall carbon nanotubes or of diamond-like carbon (DLC).

The housing parts forming electrically conductive housing contact bridges with the electrodes may advantageously be snapped into a protective sleeve or into a housing pot.

The housing parts forming the electrically conductive housing contact bridges with the electrodes may be welded into a protective sleeve or into a housing pot. The entry of gas to the measuring electrode and/or to the counterelectrode may be limited by at least one filter, which is selective for interfering gases and which is arranged especially in front of a diffusion membrane.

Exemplary embodiments of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6A is a side sectional view showing an electrode carrier with an insulating separating layer between the left and right partial segments;

FIG. 6B is a sectional view showing an electrode carrier with an insulating separating layer between the left and right partial segments.

DESCRIPTION OF THE PREFERRED EMBODIMENTS

Figures 1A, 1B:
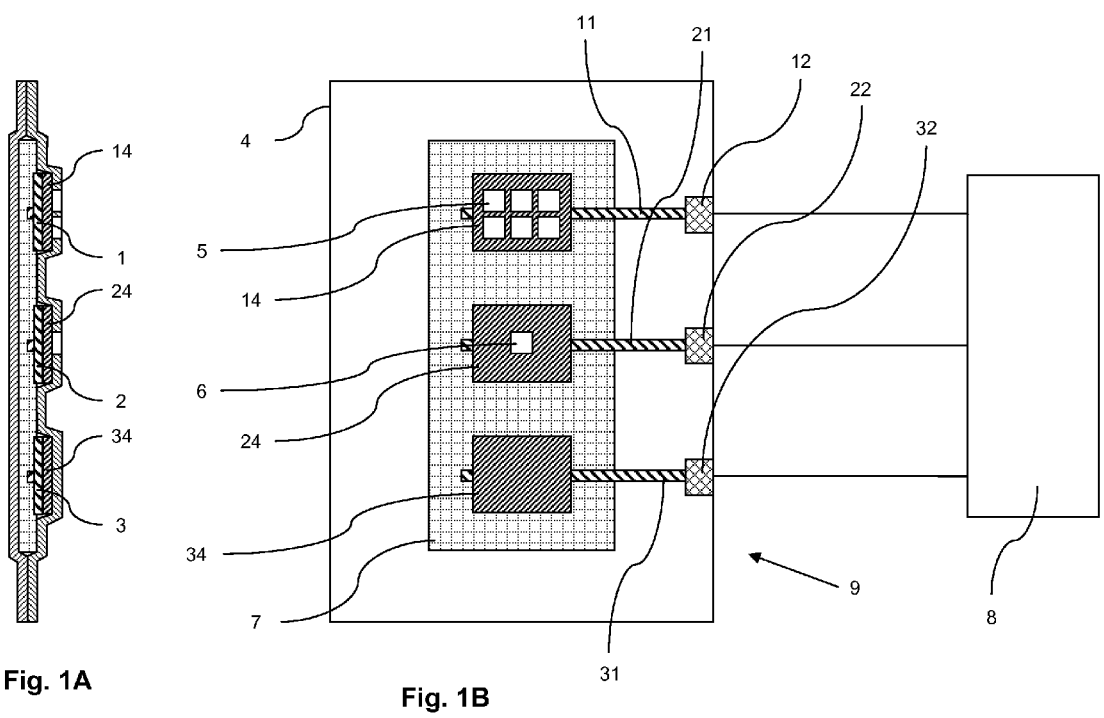
FIG. 1A is a longitudinal sectional view of a first embodiment according to the invention of an electrochemical gas sensor with strip-shaped connection lines comprising carbon nanotubes.
FIG. 1B is a top view of the first embodiment according to the invention of an electrochemical gas sensor with strip-shaped connection lines comprising carbon nanotubes.
Figure 2:
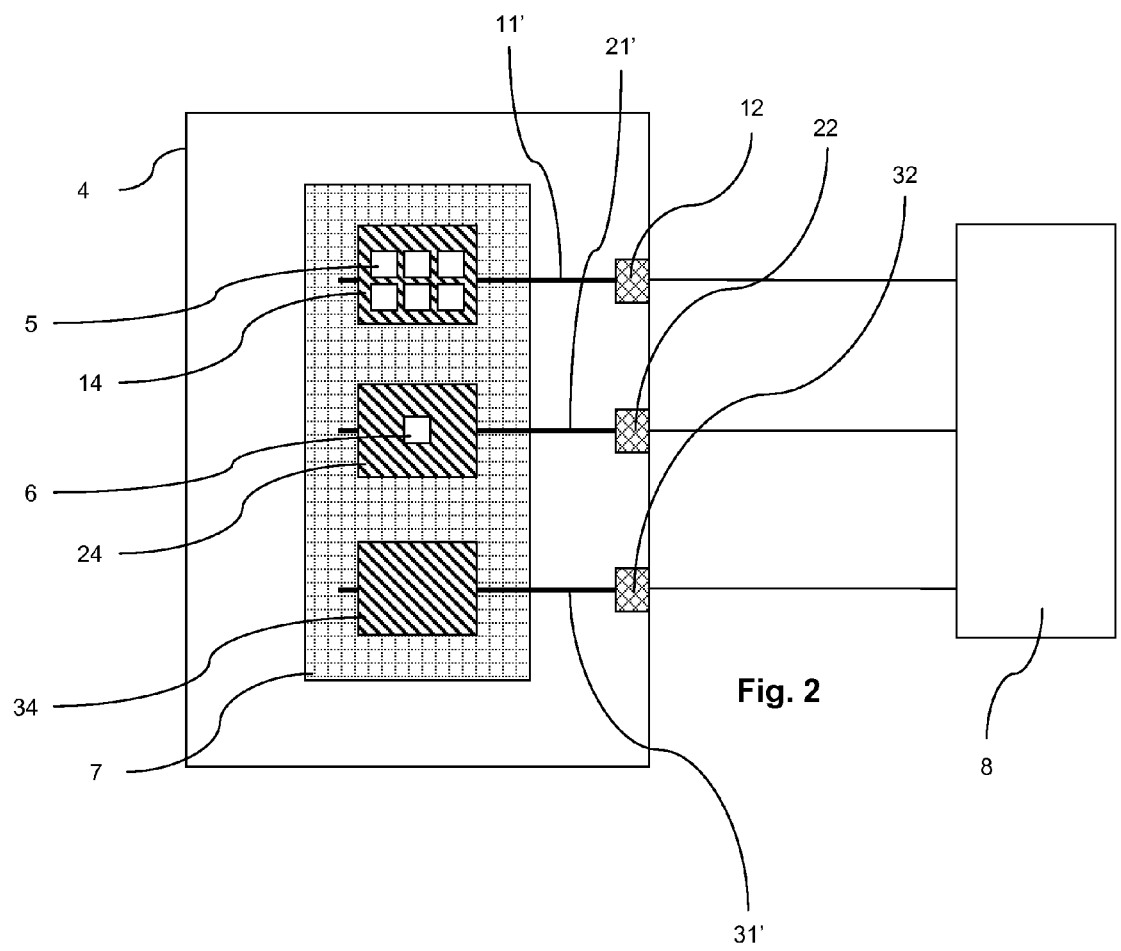
FIG. 2 is a top view showing a second embodiment according to the invention of an electrochemical gas sensor with filament-like connection lines comprising carbon nanotubes when viewed from the top and otherwise with the same components.
Figure 3:
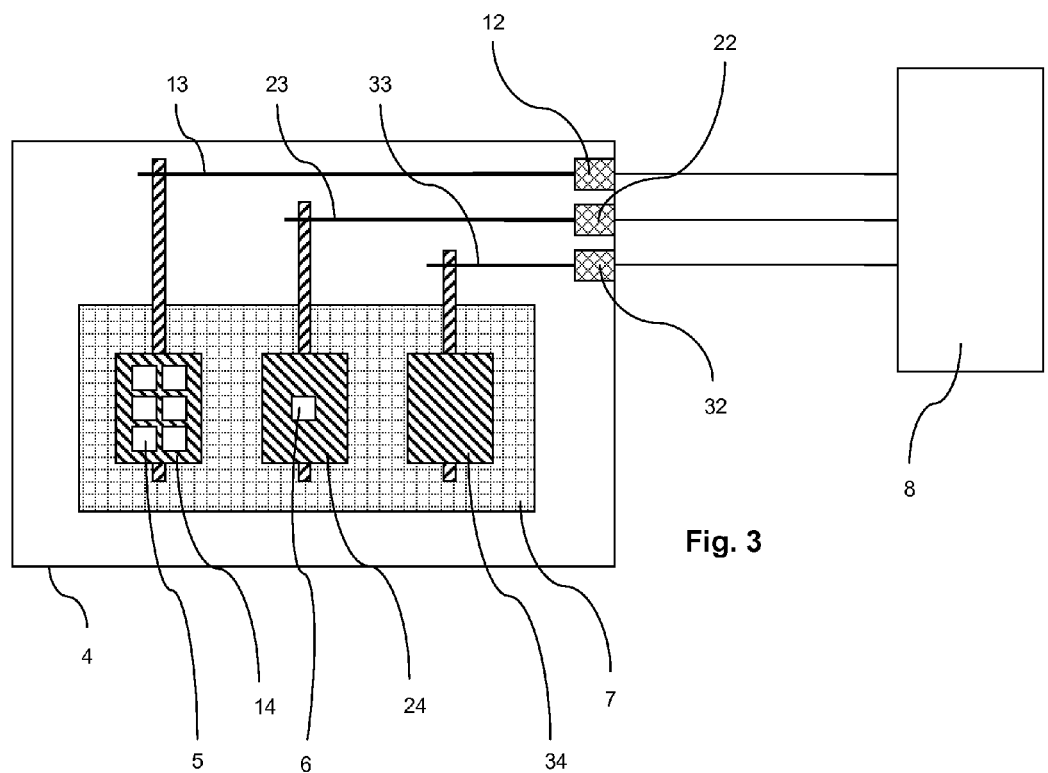
FIG. 3 is a third embodiment according to the invention of an electrochemical gas sensor with strip-shaped connection lines comprising carbon nanotubes, combined in some sections with metallic wires up to the passage through the housing.

Referring to the drawings in particular, chip-like and planar, flat electrochemical gas sensors 9, whose housing 4 is formed by welded or laminated films comprising a plastic, are shown as examples each in FIGS. 1 through 3.

The electrochemical gas sensor 9 in FIG. 1B has a measuring electrode 1 comprising diamond-like carbon (DLC), a counterelectrode 2 comprising nickel, and a reference electrode 3 comprising platinum.

All electrodes 1, 2, 3 have perfluorinated polymer diffusion membranes 14, 24, 34.

The connection lines 11, 21, 31 comprising single wall carbon nanotubes (SWCNT), which are strip-shaped here, are located between the contact pads 12, 22 and 32 and the electrodes 1, 2, 3. The gas inlet openings 5 to the measuring electrode 1 and the gas outlet openings 6 to the counterelectrode 2 are formed by corresponding patterns in the upper housing film.

The electrolyte, especially an aqueous lithium bromide solution for the electrochemical detection reaction, is taken up by a non-woven 7 designed especially as a glass fiber mat.

The measuring unit 8 is a potentiostat with an evaluating circuit and is connected to the contact pads 12, 22, 32 by means of conventional wire lines.

According to FIG. 2, the connection lines 11', 21', 31' in the housing 4 are formed entirely as filaments from carbon nanotubes.

In FIG. 3, only the sections outside the electrolyte-wetted area of the non-woven 7 (corresponding to FIG. 1) of the connection lines 13, 23, 33 in the housing 4 are made of a metal with good conductivity, such as copper, and the sections in the electrolyte are made of connection lines formed in a strip-shaped manner by a plurality of carbon nanotubes.

Figure 4:
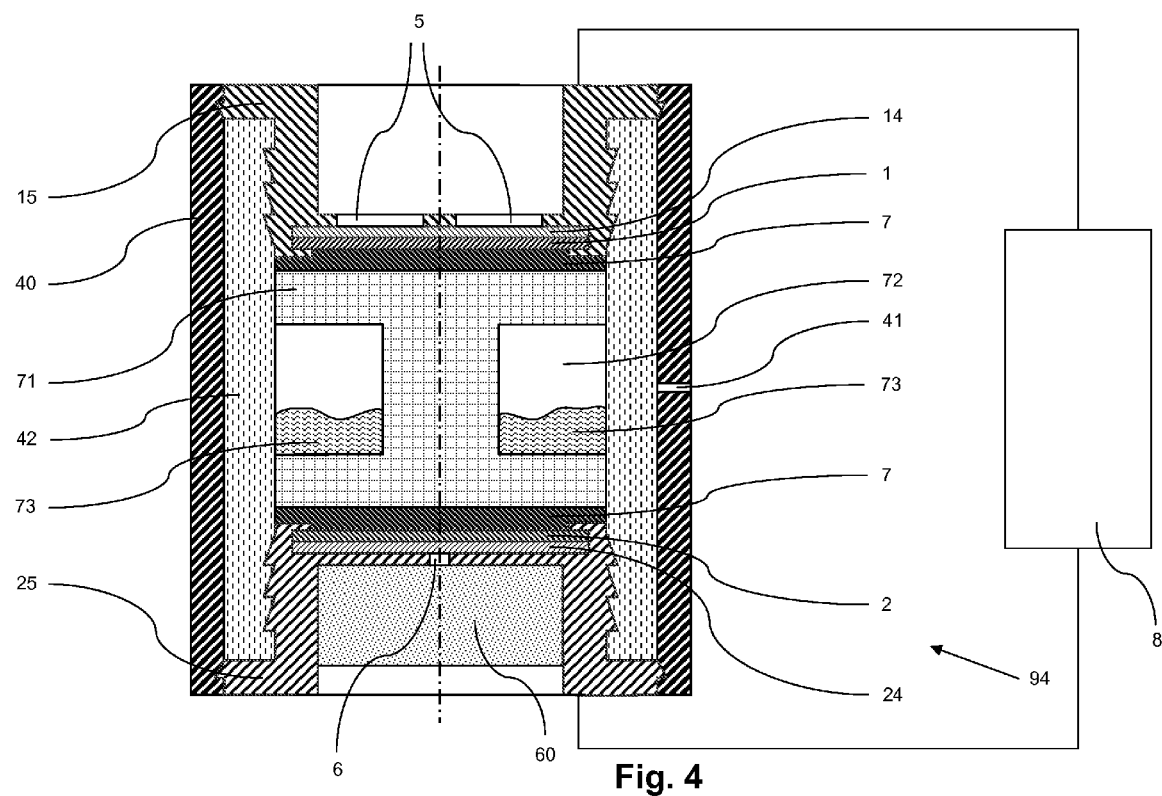
FIG. 4 is a fourth embodiment according to the invention of a cylindrical electrochemical gas sensor with electrode carriers made of a plastic that is electrically conductive due to the addition of carbon nanotubes.

FIG. 4 shows the section through a cylindrical electrochemical gas sensor 94 with the housing parts 15, 25 forming the electrode carriers, which parts 15, 25 are made of a plastic made electrically conductive by the addition of carbon nanotubes. The electrodes 1, 2, which are located on the gas-permeable diffusion membranes 14, 24, are arranged on the housing parts 15, 25 by a welding process. The electrolyte 73 necessary for the electrochemical reaction is located in the non-wovens 7 and the wick 71 and connects the electrodes 1, 2 to one another. The compensating volume 72 compensates changes in the volume of the electrolyte 73 which are due to humidity. The housing is formed by a porous PTFE cylinder 42 and a partially electrically conductive protective sleeve 40. The pressure equalization is made possible through the lateral opening 41. The gas to be measured enters via the gas inlet openings 5, and the oxygen is supplied for the counterelectrode 2 via the gas inlet opening 6.

Additional filters 60 for reducing the entry of interfering gases are optionally arranged in front of the gas inlet openings 5, 6. Diaphragms may additionally be provided for limiting the entry of the measured gas.

Figure 5A:
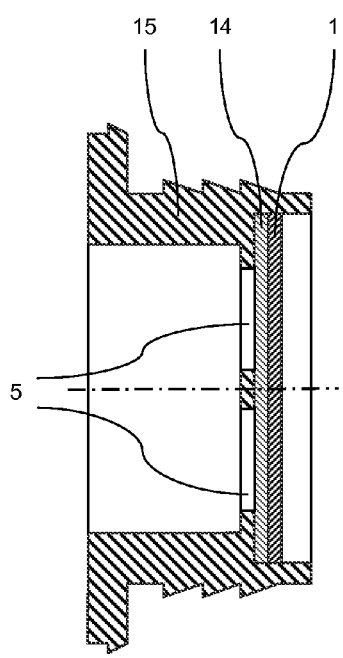
FIG. 5A is a sectional view showing the electrode carrier made of a plastic of the embodiment of FIG. 4 that is electrically conductive due to the addition of carbon nanotubes showing the state wherein the diffusion membrane-electrode composite is inserted.
Figure 5B:
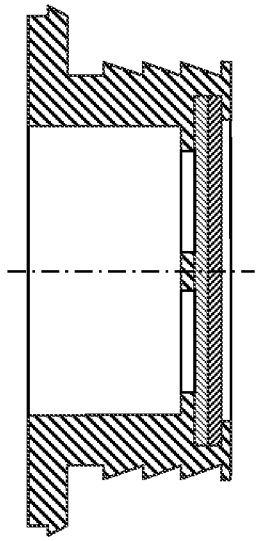
FIG. 5B is a sectional view showing the electrode carrier made of a plastic of the embodiment of FIG. 4 that is electrically conductive due to the addition of carbon nanotubes showing the state wherein the diffusion membrane-electrode composite is welded.
Figure 5C:
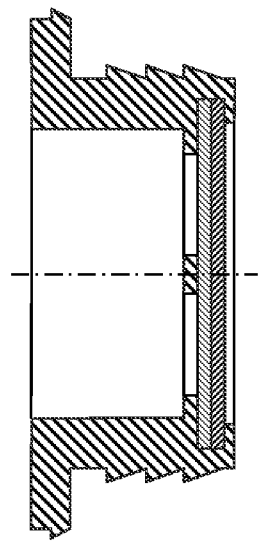
FIG. 5C is an electrode carrier made of a plastic of the embodiment of FIG. 4 that is electrically conductive due to the addition of carbon nanotubes showing the state wherein the outer welded edge was removed.

The process for producing electrode carrier-membrane-electrode composites is shown in FIG. 5:

a) Composite of electrode carrier 15, which is conductive due to the addition of carbon nanotubes, with inserted diffusion membrane 14—electrode 1;

b) the same view as in a), but with electrode welded on planarly;

c) the same view as b), but with outer welded edge removed mechanically.

FIGS. 6A and 6B shows the formation of an electrode carrier injection molded from two components with a diffusion membrane 14 and two electrodes 2, 3, which are electrically separated thereon from one another, in the form of circular segments, wherein the shaded areas 26, 36 of the electrode carrier are conductive due to single-wall carbon nanotubes contained in the plastic. The non-shaded areas 43 are non-conductive areas of the diffusion membrane 14 or of the electrode carrier, so that the two remaining housing parts 26, 36 form the counterelectrode 2 and the reference electrode 3 each with the respective electrode halves 2, 3.

Figure 7:
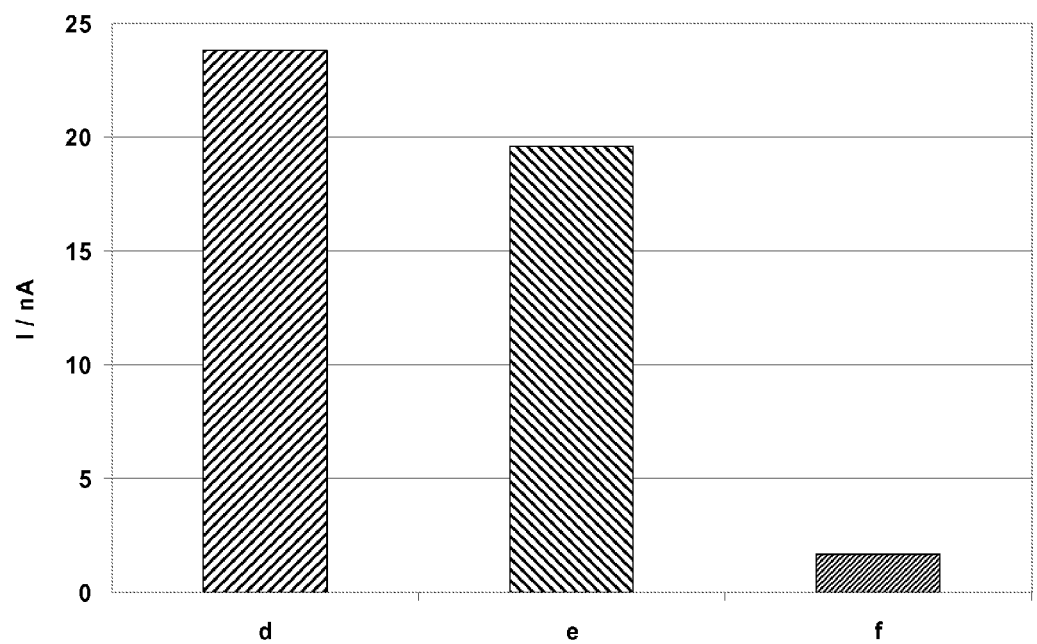
FIG. 7 is graph showing the effect of contacting on the hydrogen cross sensitivity as a diagram.

FIG. 7 shows the effect of the contacting method on the hydrogen cross sensitivity of an electrochemical gas sensor in the form of a resulting current signal:

d) Measuring electrode with platinum wire contacting as a comparison, e) platinum wire contacting without electrode, signal brought about solely by the contacting, f) measuring electrode contacted according to the present invention with strip- or filament-shaped connection lines comprising metallically conductive, single-wall carbon nanotubes or with housing contact bridges containing metallically conductive, single-wall carbon nanotubes.

While specific embodiments of the invention have been shown and described in detail to illustrate the application of the principles of the invention, it will be understood that the invention may be embodied otherwise without departing from such principles.

What is claimed is:

1. An electrochemical gas sensor comprising:
a measuring unit;
a diffusion membrane;
a housing, said measuring unit being arranged at a position outside of said housing;
an electrolyte in said housing;
a measuring electrode in contact with said electrolyte in said housing;
a counterelectrode in contact with said electrolyte in said housing;
electric connection elements from said measuring electrode and said counterelectrode to said measuring unit, at least a portion or portions of said electrical connection elements comprising carbon nanotubes or containing carbon nanotubes in said housing in a region wetted by said electrolyte.

2. An electrochemical gas sensor in accordance with claim 1, further comprising:
a first contact pad;
a second contact pad;
a first metal wire;
a second metal wire, said first contact pad and said second contact pad being in contact with an interior surface of said housing, one of said electric connection elements comprising carbon nanotubes extending from said measuring electrode to a position located outside of said electrolyte, said first metal wire connecting said one of said electric connection elements to said first contact pad, another one of said electric connection elements comprising carbon nanotubes extending from said counterelectrode to another position located outside of said electrolyte, said second metal wire connecting said another one of said electric connection elements to said second contact pad, said measuring unit being connected to said first contact pad and said second contact pad, wherein the carbon nanotubes are single-wall carbon nanotubes (SWCNT).

3. An electrochemical gas sensor in accordance with claim 1, wherein the carbon nanotubes are multi-wall carbon nanotubes (MWCNT).

4. An electrochemical gas sensor in accordance with claim 1, further comprising a contact pad located on an interior portion of said housing, wherein at least one of said measuring electrode and said counterelectrode is provided with said diffusion membrane, said housing, said electrolyte, said measuring electrode and said counterelectrode defining areas of electrolyte wetting and said portion of at least one of said electric connection elements comprising carbon nanotubes passes through said areas of electrolyte wetting, wherein said portion of at least one of said electric connection elements comprising carbon nanotubes is in contact with said electrolyte, said portion of at least one of said electric connection elements comprising carbon nanotubes being in contact with said contact pad and said measuring electrode, said measuring unit being connected to said contact pad.

5. An electrochemical gas sensor in accordance with claim 1, further comprising a diaphragm for limiting the entry of gas to be measured from the environment.

6. An electrochemical gas sensor in accordance with claim 1, wherein said portion of at least one of said electric connection elements comprising carbon nanotubes pass in the area of said housing.

7. An electrochemical gas sensor in accordance with claim 1, wherein said portion of at least one of said electric connection elements comprising carbon nanotubes comprises carbon nanotubes in a form of films, mats, strips or filaments, combined with a plastic as a composite component.

8. An electrochemical gas sensor in accordance with claim 1, wherein said measuring electrode comprises multi-wall carbon nanotubes combined with a plastic or Teflon as a binder.

9. An electrochemical gas sensor in accordance claim 1, wherein said measuring electrode comprises single-wall or double-wall carbon nanotubes or diamond-like carbon.

10. An electrochemical gas sensor in accordance with claim 1, wherein said housing comprises a protective sleeve or housing pot and said electric connection elements include housing parts forming electrically conductive housing contact bridges, said housing parts forming electrically conductive housing contact bridges with said electrodes being snapped into said protective sleeve or into said housing pot.

11. An electrochemical gas sensor in accordance with claim 1, wherein said housing comprises a protective sleeve or housing pot and said electric connection elements include housing parts forming electrically conductive housing contact bridges, said housing parts forming electrically conductive housing contact bridges with said electrodes being welded into said protective sleeve or into said housing pot.

12. An electrochemical gas sensor in accordance with claim 1, further comprising a filter and a diffusion membrane wherein the entry of gas to said measuring electrode and/or to said counterelectrode is limited by said filter, said filter being selective for interfering gases and being arranged especially in front of said diffusion membrane.

13. An electrochemical gas sensor in accordance with claim 1, wherein said housing comprises a protective sleeve or housing pot and housing parts forming electrically conductive housing contact bridges comprising said carbon nanotubes.

14. An electrochemical gas sensor according to claim 1, wherein said electrical connection elements are in a form of electrical connecting conductors or parts of said housing which form housing contact bridges, said housing contact bridges forming at least a portion of said housing.

15. An electrochemical gas sensor in accordance with claim 14, wherein only the sections of said connection lines that are in contact with the electrolyte consist of carbon nanotubes or contain carbon nanotubes.

16. An electrochemical gas sensor comprising:
a measuring unit;
a housing, said measuring unit being arranged at a location outside said housing;
a diffusion membrane;
an electrolyte located in said housing;
a measuring electrode in contact with said electrolyte located in said housing;
a counterelectrode in contact with said electrolyte located in said housing;
electric connection elements from said measuring electrode and said counterelectrode, said electric connection elements forming electric connection paths, at least a portion of said electrical connection elements comprising carbon nanotubes or containing carbon nanotubes in said housing in a region wetted by electrolyte.

17. An electrochemical gas sensor according to claim 16, wherein said electrical connection elements are in a form of electrical connecting conductors or parts of said housing which form housing contact bridges, said housing contact bridges forming at least a portion of said housing.

18. An electrochemical gas sensor in accordance with claim 16, further comprising:
a first contact pad;
a second contact pad;
a first metal wire;
a second metal wire, said first contact pad and said second contact pad being in contact with an interior surface of said housing, one of said electric connection elements comprising carbon nanotubes extending from said measuring electrode to a position located outside of said electrolyte, said first metal wire connecting said one of said electric connection elements to said first contact pad, another one of said electric connection elements comprising carbon nanotubes extending from said counterelectrode to another position located outside of said electrolyte, said second metal wire connecting said another one of said electric connection elements to said second contact pad, said measuring unit being connected to said first contact pad and said second contact pad, wherein said at least some of said electric connection element comprising carbon nanotubes comprise carbon nanotubes in a form of films, mats, strips or filaments, combined with a plastic as a composite component.

19. An electrochemical gas sensor in accordance with claim 16, further comprising a first contact pad and a second contact pad, said first contact pad and said second contact pad being in contact with an interior surface of said housing, wherein one of said electric connection elements comprising carbon nanotubes is in contact with said electrolyte and another one of said electric connection elements comprising carbon nanotubes is in contact with said electrolyte, said one of said electric connection elements comprising carbon nanotubes being in contact with said first contact pad and said measuring electrode, said measuring unit being connected to said first contact pad and said second contact pad, said another one of said electric connection elements being in contact with said second contact pad and said counterelectrode, wherein said measuring electrode comprises multi-wall carbon nanotubes combined with a plastic or Teflon as a binder.

20. An electrochemical gas sensor in accordance with claim 16, wherein said housing comprises a protective sleeve or housing pot and housing parts forming electrically conductive housing contact bridges, said housing parts forming electrically conductive housing contact bridges with said electrodes being snapped into said protective sleeve or into said housing pot.

21. An electrochemical gas sensor comprising:
a measuring unit;
a housing;
an electrolyte in said housing;
a measuring electrode in contact with said electrolyte in said housing;
a counterelectrode in contact with said electrolyte in said housing;
an electrical connection arrangement defining a signal transmission path including at least a portion consisting essentially of carbon nanotubes in contact with said electrolyte in a region adjacent to said measuring electrode and another portion consisting essentially of carbon nanotubes in contact with said electrolyte in a region adjacent to said counterelectrode.

* * * * *